United States Patent [19]  [11]  4,292,249
Nishikawa et al.  [45]  Sep. 29, 1981

[54] 25-HYDROXY-24-OXOCHOLESTANE DERIVATIVES AND PREPARATION THEREOF

[75] Inventors: Osamu Nishikawa; Kenji Ishimaru, both of Iwakuni; Toru Takeshita, Hino; Hideki Tsuruta, Iwakuni, all of Japan

[73] Assignee: Teijin Limited, Osaka, Japan

[21] Appl. No.: 121,857

[22] Filed: Feb. 15, 1980

[30] Foreign Application Priority Data

Feb. 15, 1979 [JP] Japan ................................. 54-15420
May 4, 1979 [JP] Japan ................................. 54-54154
Jun. 14, 1979 [JP] Japan ................................. 54-73956
Jul. 26, 1979 [JP] Japan ................................. 54-94183
Aug. 2, 1979 [JP] Japan ................................. 54-98106

[51] Int. Cl.³ .............................................. C07J 9/00
[52] U.S. Cl. ................................................ 260/397.2
[58] Field of Search .................................... 260/397.2; /Steroids MS File

[56] References Cited

U.S. PATENT DOCUMENTS 3,936,478 2/1976 Takeshita et al. ................. 260/397.2
4,199,577 4/1980 Takeshita et al. ................. 260/397.2

Primary Examiner—Elbert L. Roberts
Attorney, Agent, or Firm—Sughrue, Mion, Zinn, Macpeak & Seas

[57] ABSTRACT

This invention relates to novel 25-hydroxy-24-oxocholestane derivatives and a process for preparing them.

The novel 25-hydroxy-24-oxocholestane derivatives of this invention can easily be converted to 24,25-dihydroxycholecalciferol or 1α,24,25-trihydroxycholecalciferol which is known as useful for medicine controlling the calcium metabolism of warm-blooded animals. Moreover, 25-hydroxy-24-oxocholestane derivatives can be converted to novel 25-hydroxy-24-oxocholecalciferol expressed by the following formula

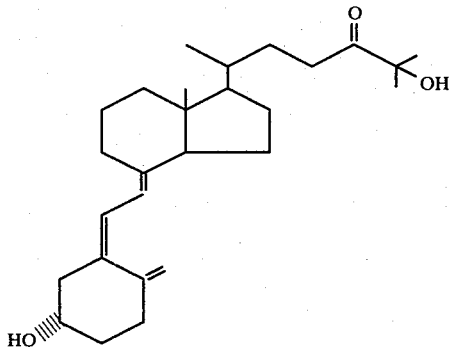

and novel 1α,25-dihydroxy-24-oxocholecalciferol of the formula

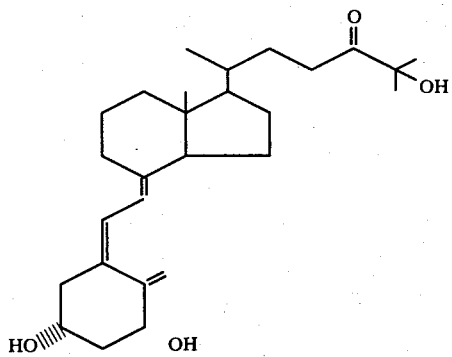

which are useful for medicine.

The new 25-hydroxy-24-oxocholestane derivatives in the present invention are very useful as the intermediates for the synthesis of a variety of active vitamin D₃.

16 Claims, 1 Drawing Figure

INTESTINAL CALCIUM ABSORPTION IN THE RATS

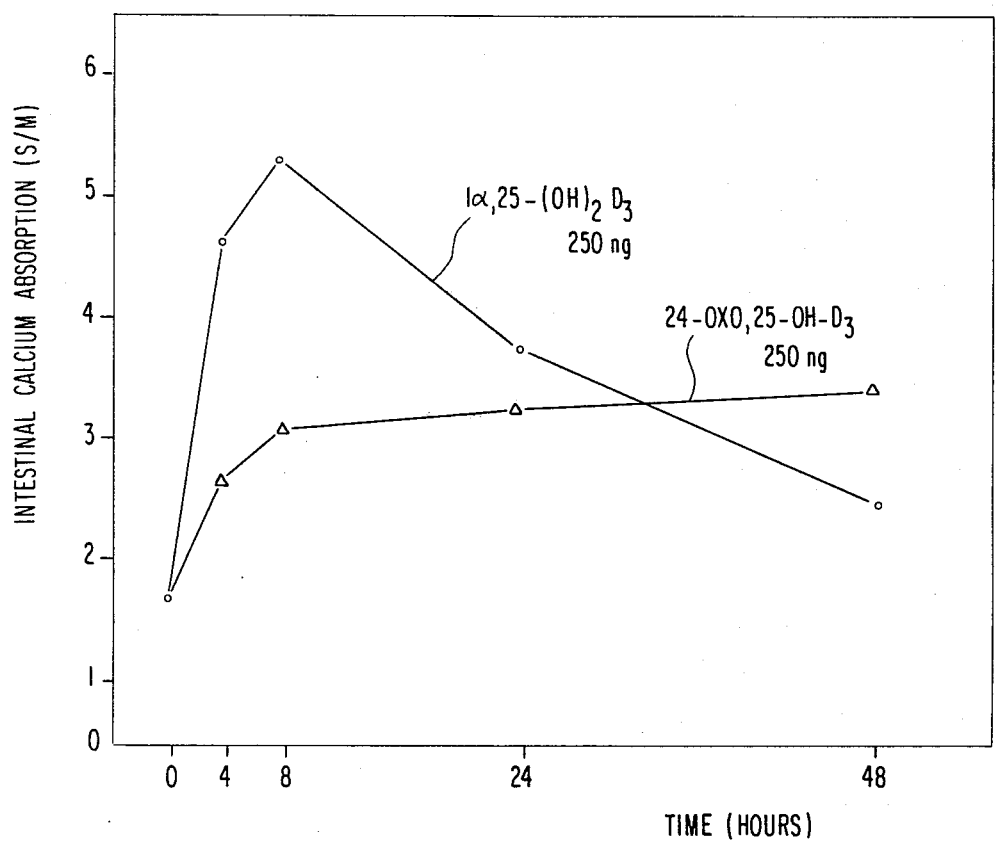

25-HYDROXY-24-OXOCHOLESTANE DERIVATIVES AND PREPARATION THEREOF

FIELD OF THE INVENTION

This invention relates to new 25-hydroxy-24-oxocholestane derivatives and a process for the preparation thereof. More specifically, this invention relates to novel 25-hydroxy-24-oxocholestane derivatives having an oxo group at the 24-position and a hydroxy group at the 25-position, which are useful intermediates convertible to active vitamin $D_3$ such as 24,25-dihydroxy cholecalciferol and $1\alpha,24,25$-trihydroxycholecalciferol.

The 25-hydroxy-24-oxocholestane derivatives, furthermore, can be converted to new active vitamin $D_3$ having an oxo group at 24-position such as 25-hydroxy-24-oxocholecalciferol and $1\alpha,25$-dihydroxy-24-oxocholecalciferol, which have a superior pharmacological activity.

Therefore, the new 25-hydroxy-24-oxocholestane derivatives in the present application are very useful as the intermediates for the synthesis of a variety of active vitamin $D_3$.

BACKGROUND OF THE INVENTION

The Chemical Pharmaceutical Bulletin 21, 457 (1973) discloses a method in which desmosterol acetate was epoxidated with m-chloroperbenzoic acid to form $3\beta$-aotoxycholest-5-ene-24,25-epoxide, which was then reacted with sulfuric acid to prepare 24,25-dihydroxycholesterol-3-acetate, or a method in which 24,25-dihydroxycholesterol-3-acetate was obtained by reacting desmosterolacetate with osmiam oxide. The above 24,25-dihydroxycholesterol-3-acetate was converted to 24,25-dihydroxycholecalciferol by a conventional method.

This method has a drawback that it involves a number of processing steps for preparing desmoterolacetate which is used as a raw material; in addition, in the former of the method the yield of 24,25-dihydroxycholesterol derived from desmosterolacetate is low. In the latter of method, osmium oxide used as reagent is expensive and toxic.

Therefore, the above mentioned method was not commercially advantageous.

On the other hand, the Biochemistry 12, 4851 (1973) discloses that 24,25-dihydroxycholecalaferol was obtained from $3\beta$-hydroxy-27-norcholest-5-ene-25-one-3-acetate. This method has a drawback that it involves a great number of processing steps.

$1\alpha,24,25$-trihydroxycholecalciferol has previously been synthesised by almost same method as mentioned above.

SUMMARY OF THE INVENTION

It is an object of this invention, therefore, to provide novel 25-hydroxy-24-oxocholestane derivatives useful for intermediates of active vitamin $D_3$ such as 24,25-dihydroxycholecalciferol, $1\alpha,24,25$-trihydroxycholecalciferal.

Another object of this invention is to provide a process for preparing 25-hydroxy-24-oxocholestane derivatives.

The 25-hydroxy-24-oxocholestane derivatives in this invention can be converted to new active vitamin $D_3$ such as 25-hydroxy-24-oxocholecalaferol, $1\alpha,25$-dihydroxy-24-oxocholecalciferol which are useful as drugs.

It is therefore a further object of this invention to provide new active vitamin $D_3$.

Other objects of this invention will become apparent from the following description.

The novel 25-hydroxy-24-oxocholestane derivatives in this invention are expressed by the following formula

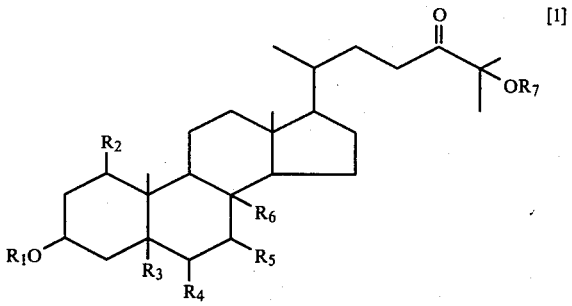

wherein $R_1$ is a hydrogen atom or a protective group; $R_2$ is a hydrogen atom, a hydroxy group or a protected hydroxy group;
$R_3$ is a hydrogen atom, $R_4$ is a hydrogen atom, a hydroxy group or a protected hydroxy group, or both $R_3$ and $R_4$ may together form a carbon-carbon bond; $R_5$ and
$R_6$ are a hydrogen atom respectively or both $R_5$ and $R_6$ may together form a carbon-carbon bond; $R_7$ is a hydrogen atom or a protective group.

BRIEF DESCRIPTION OF THE DRAWING

The FIGURE shows intestinal calcium absorption with respect to time for $1\alpha,25$-dihydroxycholecalciferol ($1\alpha,25$-$(OH)_2D_3$) and for 25-hydroxy-24-oxocholecalciferol (24-OXO,25-OH-$D_3$) as described in greater detail in Reference 5.

DETAILED DESCRIPTION OF THE INVENTION

In the new 25-hydroxy-24-oxocholestane derivatives expressed by the formula [1], $R_1$ and $R_7$ may represent a protective group and the examples of the said protective groups are listed below.

(1) Acyl groups $C_1$–$C_{12}$ aliphatic or aromatic carboxylic acid residues or their nitro-, halogen- and alkoxy-substituted derivatives, for example, acetyl, propanoyl, butanoyl, pentanoyl, capronyl, cyclohexanoyl, chloroacetyl, bromoacetyl, benzoyl, p-bromobenzoyl, p-nitrobenzoyl, ethylbenzoyl, and toluyl groups. Of these, acetyl, benzoyl and propanoyl groups are especially preferred.

(2) Groups which form ether linkages with hydroxyl groups

A tert.-butyl group, a benzyl group, a triarylmethyl group such as a triphenylmethyl group, a tetrahydropyranyl group, a methoxymethyl group, and an alkyl-substituted silyl group such as a trimethylsilyl group. Of the above protective groups, the acyl groups (1) and a tetrahydropyranyl group are especially preferred, but the invention is in no way limited to them.

$R_2$ and $R_4$ may represent a protected hydroxy group, the said group is, for example, a hydroxy group protected with the protective groups exemplified hereinabove.

R₃ and R₄ or R₅ and R₆ may together form a carbon-carbon bond. According to this definition of R₃, R₄, R₅ and R₆, the 25-hydroxy-24-oxocholestane derivatives provided according to this invention are preferably as listed below.

(i) in case where R₃ and R₄ form together a carbon-carbon bond, R₅ and R₆ are a hydrogen atom respectively.

In this case, the 25-hydroxy-24-oxocholestane derivatives are expressed by the formula

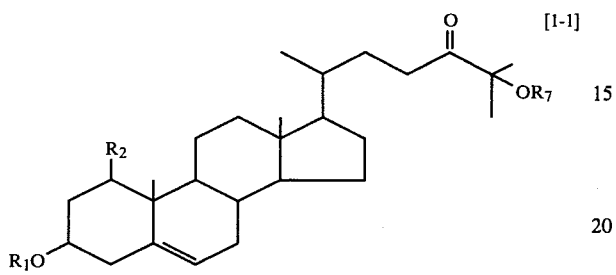

[1-1]

wherein $R_1$, $R_2$ and $R_7$ are the same as defined above in formula [1].

The 25-hydroxy-24-oxocholestane derivatives expressed by the formula [1-1] can easily be converted to 24,25-dihydroxycholecalciferol or 1α,24,25-trihydroxycholecalciferol by a sequence of reactions:
 i. reduction to form 24-hydroxy derivatives;
 ii. bromination to form 7-bromo derivatives;
 iii. dehydrobromination to form 7-dehydro derivatives;
 iv. ultraviolet ray irradiation.

The examples of the aforesaid 25-hydroxy-24-oxocholestane derivatives are listed below:
(1) 3β,25-dihydroxy-24-oxocholest-5-ene.
(2) 3β,25-dihydroxy-24-oxocholest-5-ene-3-acetate.
(3) 3β,25-dihydroxy-24-oxocholest-5-ene-3-benzoate.
(4) 3β,25-dihydroxy-24-oxocholest-5-ene-3,2'-tetrahydropyranylether.
(5) 3β,25-dihydroxy-24-oxocholest-5-ene-3-trimethylsilylether.
(6) 3β,25-dihydroxy-24-oxocholest-5-ene-3-p-toluenesulfonate.
(7) 1α,3β,25-trihydroxy-24-oxocholest-5-ene.
(8) 1α,3β,25-trihydroxy-24-oxocholest-5-ene-1,3-diacetate.
(9) 1α,3β,25-trihydroxy-24-oxocholest-5-ene-1,3-dibenzoate.
(10) 1α,3β,25-trihydroxy-24-oxocholest-5-ene-1,2',3,2'-ditetrahydropyranylether.

(ii) in case where R₃ and R₄, R₅ and R₆ forms together a carbon-carbon bond respectively:

In this case, the 25-hydroxy-24-oxocholestane derivatives are expressed by the formula

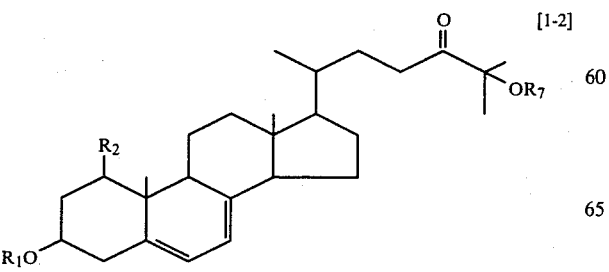

[1-2]

wherein $R_1$, $R_2$ and $R_7$ are the same as defined above in formula [1].

The 25-hydroxy-24-oxocholestane derivatives expressed in formula [1-2] can easily be converted to 24,25-dihydroxycholecalciferol or 1α,24,25-trihydroxycholecalaferol by a sequence of reactions:
 i. reduction to form 24-hydroxy derivatives;
 ii. ultraviolet ray irradiation.

The examples of the aforesaid 25-hydroxy-24-oxocholestane derivatives are as follows.
(1) 3β,25-dihydroxy-24-oxocholesta-5,7-diene.
(2) 3β,25-dihydroxy-24-oxocholesta-5,7-diene-3-acetate.
(3) 3β,25-dihydroxy-24-oxocholesta-5,7-diene-3-benzoate.
(4) 3β,25-dihydroxy-24-oxocholesta-5,7-diene-3,2'-tetrahydropyranylether.
(5) 3β,25-dihydroxy-24-oxocholesta-5,7-diene-3-trimethylsilylether.
(6) 3β,25-dihydroxy-24-oxocholesta-5,7-diene-3-p-toluenesulfonate.
(7) 1α,3β,25-trihydroxy-24-oxocholesta-5,7-diene.
(8) 1α,3β,25-trihydroxy-24-oxocholesta-5,7-diene-1,3-diacetate.
(9) 1α,3β,25-trihydroxy-24-oxocholesta-5,7-diene-1,3-dibenzoate.
(10) 1α,3β,25-trihydroxy-24-oxocholesta-5-ene-1,2',3,2'-ditetrahydropyranylether.

(iii) in case where R₃, R₅ and R₆ are a hydrogen atom respectively:

In this case, the 25-hydroxy-24-oxocholestane derivatives are expressed by the formula

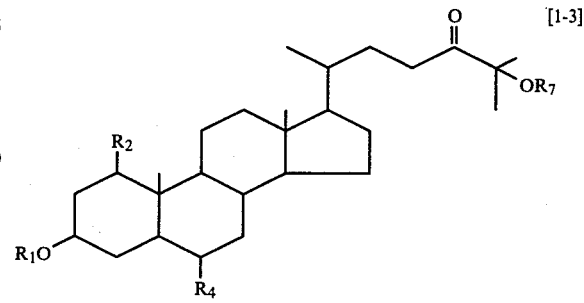

[1-3]

wherein $R_1$, $R_2$, $R_4$ and $R_7$ are the same as defined above in formula [1].

The 25-hydroxy-24-oxocholestane derivatives expressed by the formula [1-3] can easily be converted to 24,25-dihydroxycholecalaferol or 1α,24,25-dihydroxycholecalaferol by a sequence of reactions;
 i. reduction to form 24-hydroxy derivatives;
 ii. reaction according to the method disclosed in Japanese Laid-Open Patent Publication No. 112848/79 to form cholesterol derivatives;
 iii. bromination and dehydrobromination to form 7-dehydroderivatives
 iv. ultraviolet ray irradiation.

The examples of the aforesaid 25-hydroxy-24-oxocholestane derivatives are listed below.
(1) 3α,25-dihydroxy-24-oxo-5β-cholestane.
(2) 3α,25-dihydroxy-24-oxo-5β-cholestane-3-acetate.
(3) 3α,25-dihydroxy-24-oxo-5β-cholestane-3-benzoate.
(4) 25-hydroxy-24-oxo-5β-cholestane-3,2'-tetrahydropyranylether.
(5) 3α,6α,25-trihydroxy-24-oxo-5β-cholestane.

(6) 3α,6α,25-trihydroxy-24-oxo-5β-cholestane.

(7) 3α,6α,25-trihydroxy-24-oxo-5β-cholestane-6-benzoate.

(8) 3α,6α,25-trihydroxy-24-oxo-5β-cholestane-3,6-diacetate.

(9) 3α,6α,25-trihydroxy-24-oxo-5β-3,6-ditosylate.

(10) 1α,3α,25-trihydroxy-24-oxo-5β-cholestane-3,2'-6,2'-ditetrahydropyranylether.

The 25-hydroxy-24-oxocholestane derivatives in this invention are produced by oxidizing 24-oxocholestane derivatives of the formula

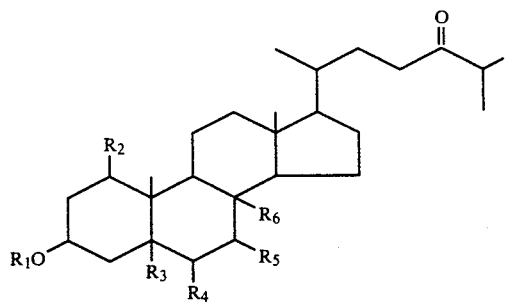

wherein $R_1$, $R_2$, $R_3$, $R_4$, $R_5$ and $R_6$ are the same as defined above in formula [1]

with molecular oxygen or molecular oxygen-containing gas in the presence of basic reagents, where required, followed by either splitting of the protective groups or protecting hydroxy groups.

In the 24-oxocholestane derivatives expressed by formula [2] used as a raw material in this invention, $R_1$, $R_2$, $R_3$, $R_4$, $R_5$ and $R_6$ are the same as defined in the formula [1]. Therefore, 24-oxocholestane derivatives used as raw material are listed below as preferable ones as in the case of 25-hydroxy-24-oxocholestane derivatives expressed by the formula [1].

(i') in case where $R_3$ and $R_4$ form together a carbon-carbon bond, $R_5$ and $R_6$ is a hydrogen atom:

In this case, the 24-oxocholestane derivatives are expressed by the formula

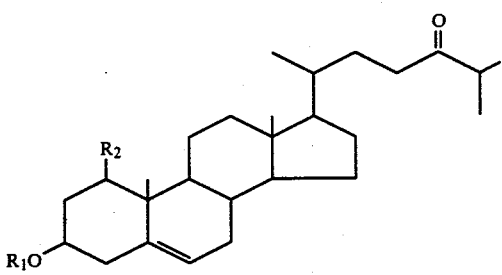

wherein $R_1$ and $R_2$ are the same as defined above in formula [1].

This compounds are prepared by the known methods (see, for example, Journal of the American Chemical Society 66, 723 (1974).

(ii') in case where $R_3$ and $R_4$, $R_5$ and $R_6$, respectively together form a carbon-carbon bond;

In this case the 24-oxocholestane derivatives are expressed by the formula

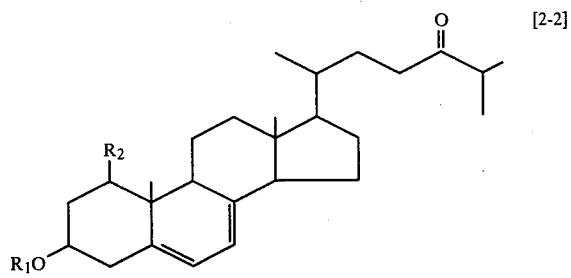

wherein $R_1$ and $R_2$ are the same as defined above in formula [1] which are synthesised by the methods disclosed in the Japanese Laid-Open Patent Publication No. 41856/79.

(iii') in case where $R_3$, $R_5$ and $R_6$ are a hydrogen atom:

In this case the 24-oxocholestane derivatives are expressed by the formula

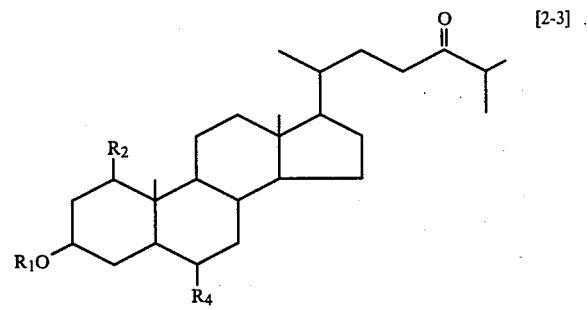

wherein $R_1$, $R_2$ and $R_4$ are the same as defined above in formula [1].

This compounds are obtained by the methods disclosed in the Japanese Laid-Open Patent Publication No.112847/79.

The examples of material compounds which are expressed by aforementioned formulas [2-1] - [2-3] are omitted here since they are self-explanatory corresponding to the examples of 25-hydroxy-24-oxocholestane derivatives expressed by formula [1].

The 25-hydroxy-24-oxocholestane derivatives of this invention are obtained by oxidizing said material compounds with molecular oxygen or molecular oxygen containing-gas in the presence of basic compounds, where required, splitting off protective groups or protecting hydroxy groups.

Basic reagents used in this invention are shown below.

(a) alcoholates such as methylate, ethyl alcoholate, n-propyl alcoholate, iso-propyl alcoholate, n-butyl alcoholate, iso-butyl alcoholate, t-butyl alcoholate, n-amyl alcoholate, hexyl alcoholate, 2-ethyl hexyl alcoholate and dodecyl alcoholate of potassium or sodium;

(b) phenolates such as potassium phenolate, sodium phenolate, potassium-2,4,6-trimethylphenolate, sodium-2,4-6-trimethylphenolate;

(c) alkali metals or alkaline earth metals such as lithum, sodium, potassium;

(d) hydride, oxide, hydroxide, carbonate, bicarbonate of alkali metals or alkaline earth metals such as sodium hydride, potassium hydride, sodium hydroxide, potassium hydroxide, calcium hydroxide, barium oxide, silver oxide, sodium carbonate, potassium carbonate, sodium bicarbonate, potassium bicarbonate;

(e) amines such as triethylamine, s-collizine, 4-dimethylaminopyridine;

(f) reaction products of cyclic glymees which are often called glyme crown compounds and alkali metals; hydrides such as NaH and KH; metals amides such as $NaNH_2$ and $KNH_2$:

(g) quarternary basic reagents such as benzyltrimethylammoniumhydroxide;

Of these basic reagents, alcoholates are preferable, more preferred basic reagents are the lower alcoholates such as methylate, ethyl alcoholate, n-propyl alcoholate, iso-propyl alcoholate, n-butyl alcoholate, iso-butyl alcoholate, t-butyl alcoholate of potassium or sodium.

It is generally desirable to use the basic reagents in an amount of 0.1 to 100 moles, preferably 1 to 10 moles, per mole of the 24-oxocholestane derivatives expressed by formula [2].

The reaction of this invention is generally carried out in an organic solvent. Any organic solvent may be used so far as if it does not interrupt the reaction of this invention.

Such organic solvent may be any of:

(a) Aliphatic hydrocarbons such as pentane, hexane, heptane, octane, nonane, decane, (b) Alicyclic hydrocarbons such as cyclopentane, methylcyclopentane, cyclohexane, methylcyclohexane, ethylcyclohexane, dimethylcyclohexane, decalin, methyldecalin, (c) Aromatic hydrocarbons such as benzene, toluene, xylene, (o.m.p. and its mixtures), ethylbenzene, trimethylbenzenes, (d) Symmetry halogenated hydrocarbons such as carbon tetrachloride, (e) alcohols such as methanol, ethanol, p-propanol, isopropanol, n-butanol, isobutanol, t-butanol, amyl alcohol, octanol, (f) halogenated hydrocarbons such as chlorobenzene, dichlorobenzene, methylenedichloride, ethylenedichloride, (g) ketones such as acetone, methyl ethyl ketone, methyl isobutyl ketone, (h) ethers such as diethyl ether, tetrahydrofuran, dioxane, (i) ester such as methyl acetate, ethyl acetate, propiolacetone, methylbenzoate, (j) sulfer-containing compounds, e.g., thioether such as diethyl thioether; sulfones such as dimethyl sulfone, tetramethyl sulfone, sulfoxides such as dimethyl sulfoxide, (k) amines such as trimethyl amine, pyridine, pyrrolidone, (l) nitro compounds such as nitrobenzene, dinitrobenzene, 2,4-dinitrotoluene, (m) cyano compounds such as acetonitrile, propionitrile, phthalonitrile, benzonitrile, (n) amides such as dimethyl formamide (DMF), dimethyl acetamide (DMAC), tetramethylurea (TMU), Hexamethyl phosphoryl amide (HMPA), N-methyl pyrroridone (NMP), diethyl formamide.

Of the aforementioned organic solvents, (c) aromatic hydrocarbons, (h) ethers and (e) alcohols are preferable.

The oxidation of 24-oxocholestane derivatives expressed by formula [2] with molecular oxygen gas with the solvent in the presence of said basic reagents is effected by stirring the reactant mixture in the closed system while making 0.5–2 moles of molecular oxygen absorbed in 1 mole of 24-oxocholestane derivatives.

The molecular oxygen-containing gas may be any of the mixtures composed of molecular oxygen and an inert gas such as nitrogen, helium, argon, methane, or propane. In this invention the reaction can be effected appropriately by using pure oxygen. Molecular oxygen or a molecular oxygen containing gas should preferably have higher partial pressure of molecular oxygen. Molecular oxygen (oxygen gas) is preferably used in this invention. The reaction can be conducted at any temperature if the reaction proceeds and the resulted compound is not decomposed or changed.

The reaction temperature is preferably in the range of 40° to 100° C., and specifically from −20° to 20° C.

The reaction time varies depending upon the type and amount of the starting materials, organic solvent, reaction temperature, etc. Generally, it is about 30 minutes to 10 hours.

Thus, the 25-hydroxy-24-oxocholestane derivatives are formed according to this present.

When the protective group of the 25-hydroxy-24-oxocholestane derivatives is an acyl group, it can be split off by deacylation using a method which comprises decomposing it in an alkali solution of an alcohol such as methanol or ethanol, or a method which comprises reductively decomposing it with $LiAlH_4$, for example, in a solvent such as an ether. Preferably, the deacylation is carried out at a temperature in the range of −10° C. to 50° C.

When the protective group forms an ether linkage with the hydroxyl group, a part of it can be easily removed by reduction or by contact with an acid or alkali.

Splitting off of protective groups is carried out preferably directly on the reaction mixture obtained in the oxidation.

When the hydroxy group of the 25-hydroxy-24-oxocholestane derivatives is protected, the formation of the protected hydroxy groups is carried out immediately after reaction mixture is obtained in the oxidation, preferably after the purification of 25-hydroxy-24-oxocholestane derivative thus obtained.

The protective group can be formed by reacting the 25-hydroxy-24-oxocholestane derivative with acetyl chloride, for example, with an inert organic solvent in the presence of an organic base as an acid acceptor. This reaction is a conventional reaction known as a Schotten-Baumann reaction. An organic base such as pyridine can be used in the above reaction as an inert organic solvent, and in this case, the use of an acid acceptor is not particularly required.

In case where the protective groups are groups which form ether linkages with hydroxyl groups, for example, the hydroxyl group can be trimethylsilylated by reacting the 25-hydroxyl-24-oxocholestane derivatives with N-trimethylsilyl imidazole in a pyridine solution at a high temperature (e.g., 50° to 110° C.).

The 25-hydroxyl-24-oxocholestane derivatives so formed can be separated and purified by column chromatography, preparative thin-layer chromatography, high speed liquid chromatography, or recrystallization. Higher purity 25-hydroxy-24-oxocholestane derivatives can be isolated by combining two or more of these purifying methods.

According to the study conducted by the present inventors, the 24-oxocholestane derivatives expressed by said formula [2] is first converted, by means of oxidation mentioned above, to 25-hydroperoxy-24-oxo-cholestane derivatives expressed by formula [3]

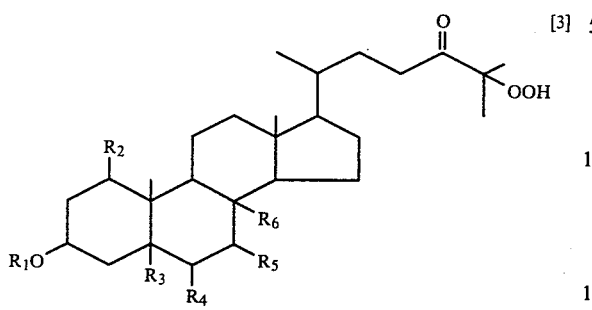

wherein $R_1$, $R_2$, $R_3$, $R_4$, $R_5$ and $R_6$ are the same as defined above in formula [1], which is followed by the conversion to 25-hydroxy-24-oxocholestane derivatives.

The present inventors through the course of the study have found that 25-hydroperoxy-24-oxocholestane derivatives expressed by formula [3] are isolated at the time of said oxidation and that 25-hydroperoxy-24-oxo-cholestane derivatives is further converted to 25-hydroxy-24-oxocholestane derivatives when subjected to the reduction.

Here the reduction is conducted in acidic or basic solution with the use of metals such as zinc, aluminium, aluminium amalgum or metal salts such as potassium iodine, and nucleophilic reagents such as triphenylphosphine, triethoxyphosphine, triethylamine, dimethylsulfide may also be used.

In order to obtain 25-hydroxy-24-oxocholestane derivatives according to the present invention, it is possible to follow the method in which 25-hydroperoxy-24-oxocholestane derivatives expressed by aforementioned formula [3] is first obtained then subjecting then to reduction. The 25-hydroxy-24-oxocholestane derivatives of this invention is prepared by subjecting 24-oxocholestane derivatives expressed by said formula [2] to the aforementioned oxidation without being isolated.

The resulting 25-hydroxyl-24-oxocholestane derivatives can be converted to a pharmacologically active vitamin $D_3$ analog, for example, 24,25-dihydroxyl-colecalciferol, 1α,24,25-trihydroxylcolecalciferol. For example, (A) 25-hydroxy-24-oxocholesterol of the formula

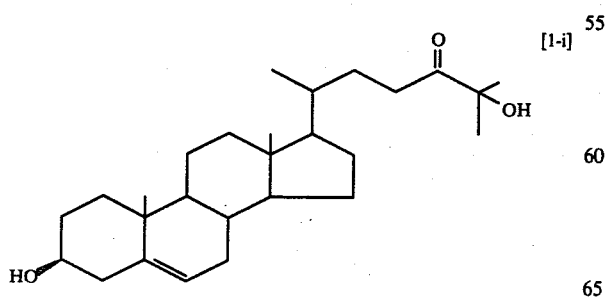

provided by this invention can be converted to 24,25-dihydroxycholecalciferol of the formula

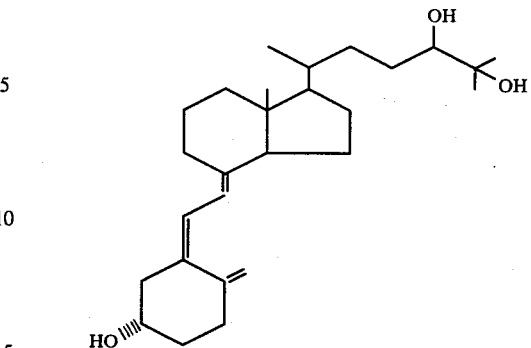

having pharmacological activity by converting it to 24,25-dihydroxycholesterol by the reduction, preparing the corresponding 5,7-diene from it in a known manner, irradiating and thermally isomerizing (see, for example, Biochemistry, 12, No. 24, 4851–4855 (1973)), (B) 25-hydroxy-24-oxocholesta-5,7-diene of the formula

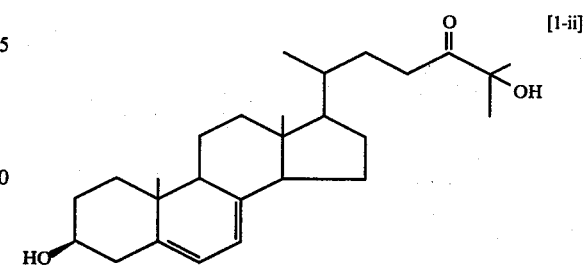

provided by this invention can be converted to 24,25-dihydroxycholecalciferol by the reduction and irradiating and thermally isomerizing, (C) 1α,25-dihydroxy-24-oxocholesta-5,7-diene of the formula

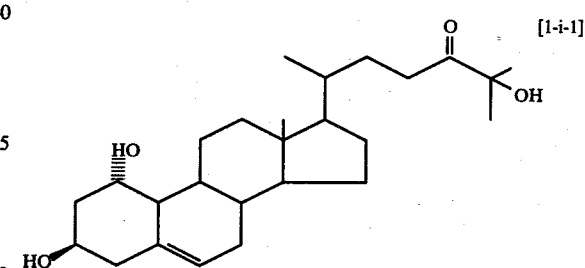

provided by this invention can be converted to 1α,24,25-trihydroxycholecalciferol of the formula

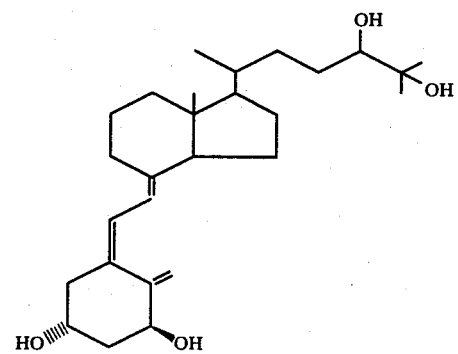

having superior pharmacological activity by: i. reduction; ii. bromination and dehydrobromination; and iii. irradiation of light and thermal isomerization (see, for example, Chemical Pharmaceutical Bulletin 23, 695–697), (D) 3α,6α,25-trihydroxy-24-oxo-5β-cholestane of the formula

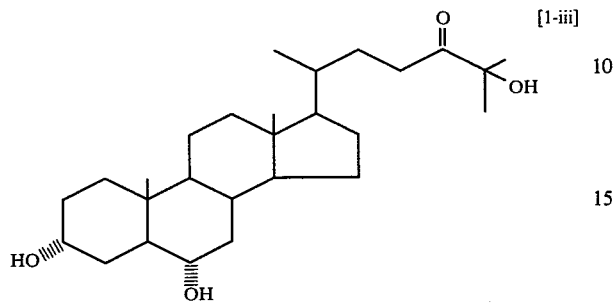

provided by this invention can be converted to 24,25-dihydroxycholecalciferol by reduction and converting it to 24,25-dihydroxycholesterol by the known method (see, for example, U.S. Pat. No. 2,781,764), preparing the corresponding 5,7-diene from it, and irradiating and thermally isomerizing.

These processes (A)–(D) have a great advantage over the known processes for preparing 24,25-dihydroxycholecalciferol or 1α,24,25-dihydroxycholecalciferol.

The reduction adopted to reduce the oxo group (=o) at the 24-position of 25-hydroxy-24-oxocholestane derivatives in the preceding (A) to (D) can be conducted under any conditions which selectively reduce the oxo group (=o) at the 24-position without bringing the reduction of double bonds.

As for such conditions of reduction, for instance, there are Pondorf reduction in which aluminiumalkoxide is used, Birth reduction which is conducted in liquid ammonia or amine in which lithuim or sodium is used, or other reduction method in which a reduction reagent is used to give hydrogen anion such as aluminium hydrides, borone hydrides, of which the methods, wherein a reduction reagent such as aluminium hydrides or borone hydrides is used, is preferable because of the simplicity of operation.

As for the aluminium hydrides, for instance, lithium aluminum hydride, sodium aluminum hydride may be mentioned and as for the borone hydride, for instance, sodium borone hydride, lithium borone hydride may be mentioned.

It is preferable to use 1.5–4 moles of such reduction reagent as aluminium hydrides borone hydrides against 1 mole of aforementioned 25-hydroxy-24-oxocholestane derivatives.

To speak of a solvent which is used in the reduction, there are ether solvents such as diethyl ether, tetrahydrofurane, alcohols such as methylalcohol, ethylalcohol, isopropylalcohol, and other solvents such as dimethyl formamide, dimethyl sulfoxide.

The reaction temperature shall preferably in the range of 5° to 50° C. and the reaction is usually completed in several hours.

Through the reduction mentioned above, the oxo group at the 24-position of novel 25-hydroxy-24-oxocholestane derivatives is reduced and the following irradiation of light and thermal isomerization provides active vitamin $D_3$.

Furthermore, the 25-hydroxy-24-oxocholestane derivatives provided by the present invention can be converted to novel 25-hydroxy-24-oxocholecalciferol of formula [4]

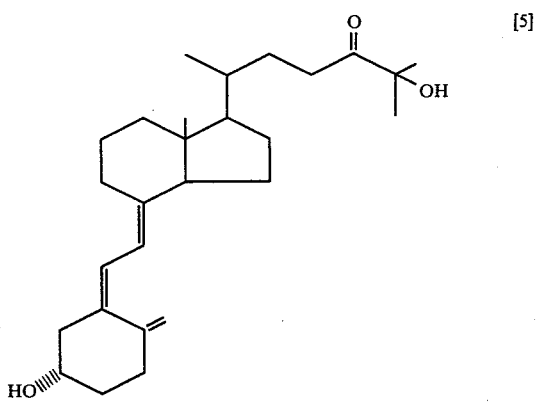

or a novel 1α,25-dihydroxy-24-oxocholecalaferol of formula [5]

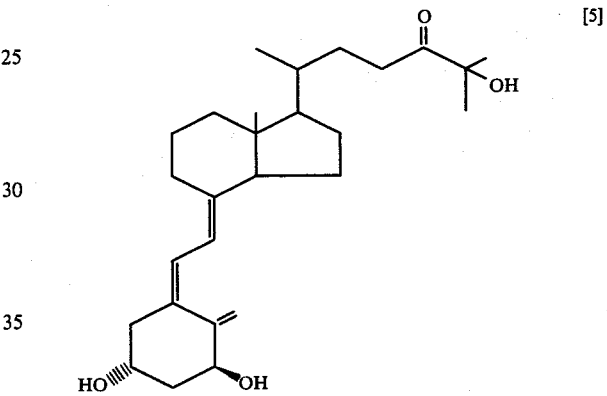

Hydroxy-24-oxocholecalciferol and 1α,25-dihydroxy-24-oxocholecalciferol are new compounds that have never been described in any literature and the process for preparation and the biological activities thereof has not been known.

According to the research works conducted by the present inventors, it has been found that the novel 25-hydroxy-24-oxocholecalciferol and 1α,25-dihydroxy-24-oxocholecalciferol have high pharmaceutical effects as agent for controlling the calcium metabolism of warm-blooded animals and that the pharmaceutical effects are superior to those of conventional vitamin $D_3$, as illustrated in the detailed animal test described in the examples later. Namely, the present inventors have now succeeded in preparation of 25-hydroxy-24-oxocholecalciferol and 1α,25-dihydroxy-24-oxocholecalciferol from the 25-hydroxy-24-oxocholestane derivatives provided by the present patent application.

For example, novel 25-hydroxy-24-oxocholecalciferol is obtained by irradiation of light and thermally isomerizing 25-hydroxy-24-oxocholesta-5,7-diene expressed by formula [1-ii].

Novel 1α,25-dihydroxy-24-oxocholecalciferol is prepared likewise from 1α,25-dihydroxy-24-oxocholesta-5,7-diene expressed by formula [1-i-1].

Said ultraviolet rays are usually employed in the range of about 200 to 360 nm in wave length and preferably from 260 to 310 nm in the present invention. A hydrocarbon or halogenated hydrocarbon, such as hexane, heptane, cyclohexane, benzene, toluene, xylene, carbon tetrachloride, 1,2-dichloroethane, 1,2-dibromoethane, as ether, such as diethyl ether, tetrahydrofuran, dioxane, such as methanol, ethanol, propanol, hexanol, cyclohexanol, are preferably used as reaction solvent.

The irradiation with ultraviolet rays is conducted at a temperature in the range of $-20°$ to $80°$ C., preferably from $-10°$ to $20°$ C. in the absence of oxygen, for example, in an argon or nitrogen atmosphere.

Thus, the irradiation with ultraviolet rays causes the cleavage between the 9- and 10-positions in the 5,7-diene compound used as a starting material to afford 25-hydroxy-24-oxoprevitamin $D_3$ or $1\alpha,25$-dihydroxy-24-oxoprevitamin $D_3$.

The resulting previtamin $D_3$ is isomerized to 25-hydroxy-24-oxocholecalciferol or $1\alpha,25$-dihydroxy-24-oxocholecalciferol of aforementioned formulas [4] and [5].

The temperature during the isomerization is preferably in the range of $10°-120°$ C. Usually, the isomerization is preferably effected in an inert organic solvent, which is the same solvent as that used in the irradiation with ultraviolet rays in practical operation.

Thus, novel 25-hydroxy-24-oxocholecalciferol or $1\alpha,25$-dihydroxy-24-oxocholecalciferol are obtained.

Resultant 25-hydroxy-24-oxocholecelafirol and $1\alpha,25$-dihydroxy-24-oxocholecalciferol have as shown in tests described below, a high pharmaceutical activity of promoting intestinal calcium absorption and raising the calcium concentration in blood.

Therefore, the above active vitamin $D_3$ prepared in accordance with the present invention can be used as a drug applicable to diseases caused by abnormal calcium metabolism.

Suitable dosages of the novel 25-hydroxy-24-oxocholecalaferol or $1\alpha,25$-dihydroxy-24-oxocholecalaferol in clinical application, based on the results of pharmacological tests conducted by the present inventors, have been found to be about 0.04–0.4 µg (about 96–960 p mole) per kilogram of the body weight of a warm-blooded animal.

The active vitamin $D_3$ of the present invention can be clinically or veterinarily applied to the following diseases:
vitamin D dependent rickets, renal osteodystrophy, hypoparathyroidism, osteoporosis, osteomalacia, Behcet's disease, malabsorption syndrome, hypocalcemia induced by liver cirrhoss, hypocalcemia induced by steatorrhoea, hypocalcemia caused by vitamin D resistant rickets, and abnormal calcium and phosphorus metabolism caused by liver failure, renal failure, gastrointestinal tract failure or parathyroid failure and related bone diseases.

Further, a composition containing 25-hydroxy-24-oxocholecalciferol or $1\alpha,25$-dihydroxy-24-oxocholecalciferol can be used in combination with other calcium metabolism regulating agents. For example, it can be applied to the treatment of Behcet's disease in combination with calcitonin.

Suitable routes of dosing include oral buccal, and parenterally, intramuscular subcutaneous, intravenous, and intrarectal administration. Dosage forms are, for example, compressed tablets, coated tablets, hard or soft elastic gelatin capsules, ethyl alcohol solutions, oil solutions, and aqueous suspensions.

The solvent for the oil solutions may be a vegetable oil such as a corn, cotton seed, coconut, almond or peanut oil, a fish liver oil, or an oily ester such as polysorbate 80.

For intrarectal administration, the above active vitamin $D_3$ may be formed into a pharmaceutical composition containing a suppository base such as cacao butter or other triglycerides. To prolong the shelf life of the pharmaceutical composition, it may advantageously include an antioxidant such as ascorbic acid, butylated hydroxyanisole, or hydroquinone.

The active vitamin $D_3$ according to this invention can be mixed with a feed for domestic animals and the feed composition for domestic animals which contains the compound can be used in amounts not to cause toxicity for the prevention of hypocalcemia of cows at or near the time of delivery, or the prevention of hypocalcemia of domestic animals with no history of hypocalcemia. When such composition are administered to poultry during oviposition, it is possible to prevent them from laying soft-shell eggs, which constitutes another characteristic feature of the active vitamin $D_3$ of the present invention.

Moreover, the novel 25-hydroxy-24-oxocholecalciferol and $1\alpha,25$-dihydroxy-24-oxocholecalciferol are useful also as intermediates for 24,25-dihydroxycholecalciferol and $1\alpha,24,25$-trihydroxycholecalciferol. Namely, the present inventors have now succeeded in preparation of 24,25-dihydroxycholecalciferol and $1\alpha,24,25$-trihydroxycholecalciferol by reducing the oxo group at 24-position in the above 25-hydroxy-24-oxocholecalciferol and $1\alpha,25$-dihydroxy-24-oxocholecalciferol respectively.

The reduction referred to in the above can be effected under the same conditions as the reduction conducted in reducing the oxo group (=o) at the 24-position of the aforesaid 25-hydroxy-24-oxocholestane derivatives, therefor no detailed description is made here as to its reduction.

The following Examples illustrate the present invention is greater detail. It should be noted that these Examples do not in any way limit the scope of the invention.

The test methods used in these Examples for the determination of the characteristics of the products were as follows:

Unless otherwise specified, NMR spectra were determined by varian EM OR JEOL PS/PFT-100 (Nippon Electronics Co., Ltd.) in deuterochloroform ($CDCl_3$) using tetramethylsilane as internal standard.

Mass spectra and high resolution mass spectra were determined by using Shimazu LKB-9000 (Shimazu Seisakusho Co., Ltd.).

UV spectra were determined by Hitachi EPS-3T (Hitachi Limited) using an ethanol solution.

The melting point was measured by means of a hot stage microscope, and the resulting values were not corrected.

EXAMPLE 1

Synthesis of 25-hydroxy-$3\beta$-[(tetrahydro-2H-pyran-2-yl)-oxy]-cholest-5-en-24-on:

1452 mg (3 m mol) of $3\beta$-[(tetrahydro-2H-pyran-2-yl)-oxy]-cholest-5-en-24-on and 504.5 mg (4.5 m mol) of potassium-t-butoxide were dissolved in a mixture of t-butyl alcohol and ethyleneglycol dimethyl ether (1:1 v/v) warming at 40° C., and while cooling the solution with ice-water to about 20° C. and stirring violently, the 3β-[(tetrahydro-2H-pyran-2-yl)-oxy]-cholest-5-en-24-on was oxidized with 72 ml of oxygen gas.

Water and ether were added to separate the reaction mixture into layers. The aqueous layer was extracted with ether. The ether extracts were combined with ether layer, and the mixture was washed successively with a dilute hydrochloric acid and a saturated aqueous solution of sodium chloride, dried over anhydrous sodium sulfate, filtered, and concentrated. The residue was dissolved in benzene, and chromatographed through a column containing silica gel as a carrier using an eluting solvent consisting of a mixture of benzene and ethyl acetate. There was obtained 291.5 mg of a purified product 25-hydroxy-3β-[(tetrahydro-2H-pyran-2-yl)-oxy]-cholest-5-en-24-on having the following characteristics.

Melting point; 146°–148° C. (N-hexane)

IR (KBr) cm$^{-1}$; 3450, 2940, 1708, 1060, 1030

NMR (CDCl$_3$, TMS), δ(ppm); 0.68 (3H, S, C-18-CH$_3$). 1.01 (3H, S, C-19-CH$_3$), 1.38 (6H, S, C-26-CH$_3$, C-27-CH$_3$), 3.78 (1H, S, C-25-OH), 3.92 (1H, bm, C-3-H), 4.70 (1H, bm, C-2′-H), 5.32 (1H, bd, C-6-H)

EXAMPLE 2

(i) Synthesis of 25-hydroperoxy-3β-[(tetrahydro-2H-pyran-2-yl)-oxy]-cholest-5-en-24-on;

1452 mg (3 m mol) of 3β-[(tetrahydro-2H-pyran-2-yl)-oxy]-cholest-5-en-24-on and 504.5 mg (4.5 m mol) of potassium-t-butoxide were dissolved in a mixture of t-butyl alcohol and ethyleneglycol dimethyl ether (1:1 v/v) warming at 40° C., and while cooling the solution with ice-water to about 0° C. and stirring violently, 3β-[(tetrahydro-2-H-pyran-2-yl)-oxy]-cholest-5-en-24-on was oxidized with 70 c.c. of oxygen gas.

After the reaction, water and a small amount of acetic acid were added successively to neutralize the solution to pH 6–7. The reaction mixture was then extracted with ethyl acetate.

The ethylacetate extract was washed with a saturated solution of sodium chloride, dried over anhydrous sodium sulfate, filtered and concentrated. The residue was chromatographed succesively through a column containing silicagel as a carrier using an eluting solvent consisting of a mixture of n-hexane and benzene, and through a commercially available plate for preparative thin-layer chromatography (Silica gel as a carrier, a product of Merch Company, 20 cm×20 cm×0.5 mm) using an eluting solvent consisting a mixture of benzene and ethyl acetate. There was obtained 95.6 mg of 25-hydroperoxy-3β-[(tetrahydro-2H-pyran-2-yl)-oxy]-cholest-5-en-24-on having the following characteristics.

Melting point; 130°–131° C. (n-hexane)

IR (CHCl$_3$) cm$^{-1}$; 2925, 2850, 1708, 1460, 1373, 1125, 1070, 1015

NMR (CDCl$_3$, TMS), δ(ppm); 0.68 (3H, S, C-18-CH$_3$), 1.01 (3H, S, C-19-CH$_3$), 1.39 (6H, S, C-26-CH$_3$, C-27-CH$_3$), 3.8–4.1 (1H, bm, C-3-H), 4.70 (1H, bm, C-2,3-H), 5.32 (1H, bm, C-6-H)

(ii) Synthesis of 25-hydroxy-3β-[(tetrahydro-2H-pyran-2-yl)-oxy]-cholest-5-en-24-on;

258 mg (0.5 m mol) of 25-hydroperoxy-3β-[(tetrahydro-2H-pyran-2-yl)-oxy]-cholest-5-en-24-on was dissolved in 5 ml of benzene.

To the solution 1 ml of a satulated aqueous solution of potassium iodide and 30 ml of acetic acid were added. After substituting air for carbondioxide gas, the reaction was carried out at room temperature in the dark for 15 minutes.

After the reaction, 30 ml of water was added and the resulting iodine was titrated with 8.8 ml of a 0.1 N aquious solution of sodium thiosulfate using an aqueous solution of starch as a indicator.

The yield of this reaction was 88% being based on the iodometric titration.

After the titration the mixture was extracted with 50 ml of ethyl acetate. The ethylacetate extract was washed successively with a saturated aqueous solution of sodium hydrogen carbonate and a saturated aqueous solution of sodium chroride, dried over anhydrous sodium sulfate, filtered and concentrated. 231 mg of the resulting residue was a mixture of 25-hydroxy-24-oxocholesterol and 25-hydroxy-3β-[(tetrahydro-2H-pyran-2-yl)-oxy]-cholest-5-en-24-on. These products showed the same characteristics as authentic samples respectively.

EXAMPLE 3

Synthesis of 25-hydroxy-3β-[(tetrahydro-2H-pyran-2-yl)-oxy]-cholest-5-en-24-on;

258 mg (0.5 m mol) of 25-hydroperoxy-3β-[(tetrahydro-2H-pyran-2-yl)-oxy]-cholest-5-en-24-on was dissolved in 10 ml of benzene, and while cooling the solution with ice-water to about 5° C. and stirring, 131 mg (0.5 m mol) of triphenylphosphine dissolved in 10 ml of benzene was added.

After the addition the mixture was stirred at room temperature for 30 minutes.

The benzene was evaporated off at reduced pressure, and the residue was chromatographed through a commercially available plate for preparative thin-layer chromatography (Silica gel as a carrier, a product of Merch Company 20 cm×20 cm×0.5 mm) using an eluting solvent consisting a mixture of benzene and ethyl acetate.

There was obtained 236 mg of a purified product (94%). This product showed the same melting point, IR and NMR spectrum data as the 25-hydroxy-3β-[(tetrahydro-2H-pyran-2-yl)-oxy]-cholest-5-en-24-on obtained in Example 1.

EXAMPLE 4

Synthesis of 25-hydroxy-24-oxocholesterol-3β-acetate;

1702 mg (3.85 m mol) of 24-oxocholesterol-3β-acetate and 647 mg (5.77 m mol) of potassium-t-butoxide were dissolved in a mixture of t-butyl alcohol and ethyleneglycol dimethyl ether (1:1 V/V), warming at 40° C., and while cooling the solution with ice-water to about 20° C. and stirring violently, the 24-oxocholesterol-3β-acetate was oxidized with 88 ml of oxygen gas. Water and ether were added to separate the reaction mixture into layers.

The aqueous layer was extracted with ether. The ether extracts were combined with ether layer, and the mixture was washed successively with dilute hydrochloric acid and a saturated aqueous solution of sodium chloride, dried over anhydrous sodium sulfate, filtered and concentrated.

The residue was dissolved in benzene, and chromatographed through a column containing silicagel as a carrier using an eluting solvent consisting of a mixture of benzene and ethyl acetate. There were obtained 72 mg of 25-hydroxy-24-oxocholesterol-3β-acetate and 299 mg of 25-hydroxy-24-oxocholesterol having the following characteristics.

*25-hydroxy-24-oxocholesterol-3β-acetate;

Melting point; 141°–143° C. (N-hexane)

IR (KBr) cm$^{-1}$; 3430, 2940, 1730, 1710, 1465, 1365, 1248, 1035

NMR (CDCl$_3$, TMS), δ (ppm); 0.68 (3H, S, C-18-CH$_3$), 1.01 (3H, S, C-19-CH$_3$), 1.38 (6H, S, C-26-CH$_3$, C-27-CH$_3$), 2.02 (3H, S, C-3-OCOCH$_3$), 4.60 (1H, bm, C-3-H), 5.36 (1H, bd, C-6-H)

High resolution mass spectrum;

M$^+$-CH$_3$CO$_2$H 398.3182 (C$_{27}$H$_{42}$O$_2$)

*25-hydroxy-24-oxocholesterol;

Melting point; 168°–170° C. (benzene)

IR (KBr) cm$^{-1}$; 3425, 2925, 1708, 1460, 1370, 1050

NMR (CDCl$_3$, TMS), δ (ppm); 0.68 (3H, S, C-18-CH$_3$), 1.01 (3H, S, C-19-CH$_3$), 1.38 (6H, S, C-26-CH$_3$, C-27-CH$_3$), 3.60 (1H, bm, C-3-H), 5.34 (1H, bd, C-6-H)

High resolution mass spectrum;

M$^+$ 416.3380 (C$_{27}$H$_{44}$O$_3$)

EXAMPLE 5

(i) Synthesis of 25-hydroperoxy-24-oxocholesterol; 1200 mg (3 m mol) of 24-oxocholesterol and 504.5 mg (4.5 m mol) of potassium-t-butoxide were dissolved in a mixture of t-butyl alcohol and ethyleneglycol dimethylether (1:1 V/V) warming at 40° C., and while cooling the solution with ice-water to about 0° C. and stirring violently, 24-oxocholesterol was oxidized with 70 c.c. of oxygen gas. After the reaction, water and a small amount of acetic acid were added successively to neutralize the solution to pH of 6–7. The reaction mixture was then extracted with ethyl acetate. The ethyl acetate extract was washed with a saturated solution of sodium chloride, dried over anhydrous sodium sulfate, filtered and concentrated.

The residue was chromatographed successively through a column containing silicagel as a carrier using an eluting solvent consisting of a mixture of benzene and ethyl acetate, and through a commercially available plate for preparative thinlayer chromatography (Silica gel as a carrier, a product of Merch Company, 20 cm×20 cm×0.5 mm) using an eluting solvent consisting a mixture of benzene and ethyl acetate.

There was obtained 58.5 mg of 25-hydroperoxy-24-oxocholesterol having the following characteristics.

Melting point; 145.5°–147° C. (n-hexane-ethylalcohol)

IR (KBr) cm$^{-1}$; 3420, 2940, 1708, 1465, 1375, 1054

NMR (CDCl$_3$, TMS), δ (ppm); 0.68 (3H, S, C-18-CH$_3$) 1.01 (3H, S, C-19-CH$_3$), 1.38 (6H, S, C-26-CH$_3$, C-27-CH$_3$), 3.4–3.7 (1H, bm, C-3-H), 5.32 (1m, bm, C-6-H)

High resolution mass spectrum;

M$^+$-(CH$_3$)$_2$CO; 374.2786 (C$_{24}$H$_{38}$O$_3$)

(ii) Synthesis of 25-hydroxy-24-oxocholesterol;

26 mg of 25-hydroperoxy-24-oxocholesterol was dissolved in 4 ml of acetic acid.

To the solution 60 mg of zinc powder was added, and the resulting mixture was stirred at room temperature for 18 hours.

Water and ethyl acetate were added to separate the reaction mixture into layers, and the resulting zinc acetate was separated by filtration.

The ethyl acetate layer was washed successively with a saturated aqueous solution of sodium hydrogen carbonate and a saturated aqueous solution of sodium chloride, dried over anhydrous sodium sulfate, filtered and concentrated to afford 27 mg of 25-hydroxy-24-oxocholesterol. The product, purified by recrystallization using benzene, showed the same melting point, IR and NMR spectrum data as the 25-hydroxy-24-oxocholesterol obtained in Example 4.

Reference 1

Synthesis of 24,25-dihydroxycholesterol; 386 mg (0.93 m mol) of 25-hydroxy-24-oxocholesterol 5-en was dissolved in 25 ml of methanol and 71 mg of sodium borohydride was added to the solution at 20° C. Stirring was continued for 3 hours at room temperature, a small amount of aqueous hydrochloric acid was added to decompose the excess sodium borohydride and the methanol was evaporated off under reduced pressure.

The residue was extracted with ethyl acetate, the extraction was washed with a saturated aqueous solution of sodium hydrogen carbonate and water, dried over anhydrous sodium sulfate, filtered and concentrated.

390 mg of 24,25-dihydroxycholesterol was obtained.

This compound shows the following physical properties:

Melting point; 183° C.

IR (KBr) cm$^{-1}$; 3400, 2920, 1460, 1373, 1055

NMR (CDCl$_3$, TMS), δ (ppm); 0.69 (3H, S, C-18-CH$_3$) 1.01 (3H, S, C-19-CH$_3$) 1.15 and 1.21 (6H, C-26-CH$_3$ and C-27-CH$_3$) 3.20–3.40 (2H, C-3-H and C-24-H) 5.34 (1H, bd, C-6-H)

High resolution mass spectrum;

M$^+$=418.3465 (C$_{27}$H$_{46}$O$_3$)

EXAMPLE 6

Synthesis of 3α,6α,25-trihydroxy-24-oxo-5β-cholestane;

(i) 1704 mg (3 m mol) of 24-oxo-3α,6α-di-[(tetrahydro-2H-pyran-2-yl)-oxy]-5β-cholestane and 504.5 mg (4.5 m mol) of potassium-t-butoxide were dissolved in a mixture of t-butyl alcohol and ethyleneglycol dimethyl ether (1:1 V/V), warming at 40° C., and while cooling the solutions with ice-water to about 0° C. and stirring violently, the 24-oxo-3α,6α-di-[(tetrahydro-2H-pyran-2-yl)-oxy]-5β-cholestane was oxidized with 80 ml of oxygen gas. 3 g of zinc powder and 65 ml of acetic acid were added, and the resulting hydroperoxide was reductively decomposed at room temperature for 20 hours.

The resulting zinc acetate was separated by filtration and the acetic acid phase was diluted with 200 ml of water. The aqueous solution was extracted with ethyl acetate. The ethyl acetate extract was washed successively with a saturated aqueous solution of sodium hydrogen carbonate and a saturated aqueous solution of sodium chloride, dried over anhydrous sodium sulfate, filtered and concentrated.

The resulting crude product, 25-hydroxy-24-oxo-3α,6α-di-[(tetrahydro-2H-pyran-2-yl)-oxy]-5β-cholestane without purification, was subjected to hydrolysis reaction. Specifically, the crude product was dissolved in methanol. To the solution was added dropwise small amount of conc. hydrochloric acid. The mixture was stirred at room temperature for 1 hour. After the reaction, the reaction mixture was concentrated at reduced pressure. To the residue, water and ethyl acetate was added to separate the reaction mixture into layers. The aqueous layer was extracted with ethyl acetate. The ethyl acetate extracts were combined with ethyl acetate layer, and the mixture was washed successively with a saturated aqueous solution of sodium hydrogen carbonate and a saturated aqueous solution of sodium chloride, dried over anhydrous sodium sulfate, filtered and concentrated. The residue was dissolved in benzene, and chromatographed through a column containing silica gel as a carrier using an eluting solvent consisting of a mixture of benzene and ethyl acetate. There was obtained 501 mg of $3\alpha,6\alpha,25$-trihydroxy-24-oxo-$5\beta$-cholestane having the following characteristics.

Melting point; 189°–191° C. (ethylacetate)
IR (KBr) cm$^{-1}$; 3400, 2925, 2850, 1705, 1460, 1375, 1035
NMR (CDCl$_3$, TMS), $\delta$ (ppm); 0.65 (S, 3H, C-18-CH$_3$), 0.91 (S, 3H, C-19-CH$_3$), 1.38 (S, 6H, C-26-CH$_3$, C-27-CH$_3$), 3.4–4.2 (bm, 2H, C-3-H, C-6-H)
High resolution mass spectrum;
M$^+$-H$_2$O=416.3278 (C$_{27}$H$_{44}$O$_3$)

EXAMPLE 7

Synthesis of $1\alpha,25$-dihydroxy-24-oxocholesterol;

1248 mg (3 m mol) of $1\alpha$-hydroxy-24-oxocholesterol and 504.5 mg (4.5 m mol) of potassium-t-butoxide were dissolved in a mixture of t-butyl alcohol and ethyleneglycol dimethyl ether (1:1 V/V), warming at 40° C., and while cooling the solution with ice-water to about 0° C., and stirring violently, the $1\alpha$-hydroxy-24-oxocholesterol was oxidized with 81 ml of oxygen gas. 3 g of zinc powder and 65 ml of acetic acid were added, and the resulting hydroperoxide was reductively decomposed at room temperature for 24 hours. The resulting zinc acetate was separated by filtration and the acetic acid phase was diluted with 200 ml of water. The aqueous solution was extracted with ethyl acetate.

The ethyl acetate extract was washed successively with a satulated aqueous solution of sodium hydrogen carbonate and satulated aqueous solution of sodium chloride, dried over anhydrous sodium sulfate, filtered and concentrated.

The residue was chromatographed through a column containing silica gel as a carrier using an eluting solvent consisting of a mixture of benzene and acetone.

There was obtained 315 mg of $1\alpha,25$-dihydroxy-24-oxocholesterol having the following characteristics.

Melting point; 192°–194° C. (ethyl acetate)
IR (KBr) cm$^{-1}$; 3425, 2940, 1705, 1050
NMR (CDCl$_3$, TMS), $\delta$ (ppm); 0.69 (3H, S, C-18-CH$_3$), 1.04 (3H, S, C-19-CH$_3$), 1.39 (6H, S, C-26-CH$_3$, C-27-CH$_3$), 3.7–3.9 (1H, bm, C-3-H), 3.9–4.2 (1H, bm, C-1-H), 5.58 (1H, bm, C-6-H)
High resolution mass spectrum;
M$^+$ 432.3175 (C$_{27}$H$_{44}$O$_4$)

Reference 2

Synthesis of $1\alpha,24,25$-trihydroxycholesterol; 20 mg of $1\alpha,25$-dihydroxy-24-oxocholesterol was dissolved in 42 ml of methanol and 21 mg of sodium borohydride was added to the solution at room temperature under an argon atmosphere. Stirring was continued for 5 hours at 30° C., a small amount of 10% aqueous acetic acid was added to decompose the excess sodium borohydride and the methanol was evaporated.

The residue was separated and purified by means of preparative thin layer chromato graphy (developing with 10% methanol-chloroform) to afford 13 mg of $1\alpha,24,25$-trihydroxycholesterol having the following physical properties:

Melting point; 198°–200° C.
NMR (C$_5$D$_5$N); 0.81 (3H, S, C-18-CH$_3$)
1.07 (3H, S, C-19-CH$_3$)
1.38 (6H, S, C-26-CH$_3$ and C-27-CH$_3$)
3.47 (1H, m, C-24-H)
4.01 (1H, m, C-1-H)

EXAMPLE 8

(i) Synthesis of 24-ethylenedioxycholesterol;

27 g of 24-oxocholesterol was dissolved in 717 ml of anhydrous benzene. To the solution were added 179 ml of ethylene glycol and 358 mg of p-toluen sulfonic acid. The mixture was stirred and heated at a bath temperature of 105° C. for 20 hours in a flask equipped with receiver capable of mesuring water in which was added a molecular sieve. Water was added to separate the reaction mixture into layers. The aqueous layer was extracted with benzene.

The benzene extract was combined with the benzene layer, and the mixture was washed with a 5% aqueous solution of sodium hydrogen carbonate and a satulated aquous solution of sodium chloride, dried over anhydrous sodium sulfate, filtered and concentrated. The resulting solid product, 29 g of 24-ethylenedioxy cholesterol, without purification, was subjected to a acetylation reaction.

(ii) Synthesis of 24-ethylenedioxy cholesterol-$3\beta$-acetate;

29 g of 24-ethylenedioxy cholesterol was dissolved in 100 ml of pyridine. To the solution was added 53 ml of acetic anhydride. The mixture was stirred and heated at a bath temperature of 60° C. for 1 hour. After the reaction, water was added, and extracted with ether. The ether extract was washed successively with a 2N-hydrochloric acid, a 5% aqueous solution of sodium hydrogen carbonate and a saturated aqueous solution of sodium chloride, dried over anhydrous sodium sulfate, filtered and concentrated.

The resulting oily product, was isolated and purified by recrystallizing with methyl alcohol to afford 20.6 g of 24-ethylenedioxy cholesterol-$3\beta$-acetate.

(iii) Synthesis of $3\beta$-hydroxy-24-oxocholesta-5,7-dien;

20.5 g of 24-ethylenedioxycholesterol-$3\beta$-acetate was dissolved in 624 ml of hexane. The solution was heated at a bath temperature of 95° C., stirred and to the solution 6.12 g of 1.3-dibromo-5,5-dimethylhydantoine was added.

The mixture was stirred violently and heated under the irradiation with infrared rays for 15 minutes. The reaction mixture was cooled, and the resulting crystals were removed by filtration. The filtrate was concentrated at reduced pressure to afford a yellow oily substance, crude bromo-compounds of 24-ethylenedioxy cholesterol-$3\beta$-acetate. To this substance was added 250 ml of xylene. The resulting solution was added dropwise over the course of about 15 minutes to a solution of 500 ml of xylene and 77 ml of s-collidine under reflux, and the reaction was performed for an additional 20 minutes. The reaction mixture was cooled, and the resulting crystals were removed by filtration.

The filtrate was concentrated at reduced pressure to afford a yellow oily substance, crude dehydro compounds of 24-ethylenedioxycholesterol-3β-acetate. This substance was dissolved in 1370 ml of acetone. To the solution, 8 g of p-toluene sulfonic acid was added, and the mixture was stirred at room temperature for 3 hours. The mixture was concentrated. The resulting residue was dissolved in ethyl acetate, and the ethyl acetate solution was washed with a 5% aqueous solution of sodium hydrogen carbonate and a saturated aqueous solution of sodium chloride, dried over anhydrous sodium sulfate, filtered and concentrated to afford a crude residue containing 3β-acetoxy-24-oxo cholesta-5,7-dien. This residue was dissolved in benzene. To the solution was added 2060 ml of a 1% methyl alcohol solution of potassium hydroxide.

The mixture was stirred at room temperature for 20 hours.

After the reaction, the reaction mixture was concentrated, and water was added to separate into layers. The aqueous layer was extracted with ethyl acetate. The ethyl acetate extract was combined with the benzene layer, and the mixture was washed successively with a dilute hydrochloric acid and a saturated aqueous solution of sodium chloride, dried over anhydrous sodium sulfate filtered and concentrated. The residue was dissolved in benzene and chromatographed through a column containing silica gel as a carrier using an eluting solvent consisting of a mixture of benzene and ethyl acetate.

The resulting crude product, 3β-hydroxy-24-oxocholesta-5,7-dien, was chromatographed through a commercially available plate for preparative thin-layer chromatography (Silica gel, a product of Merch Company, 20 cm×20 cm×0.5 mm) which was immersed in a solution of silver nitrate in acetonitrile to impregnate it in an amount of about 2% by weight as silver nitrate. There was obtained a purified product having the following characteristics.

IR (KBr) cm$^{-1}$; 3425, 2925, 1708, 1462, 1377, 1060, 1035

U V (EtOH: $\lambda_{max}$)nm; 294, 282, 271, 262

Mass spectrum; M+ 398

(iv) Synthesis of 3β,25-dihydroxy-24-oxocholesta-5,7-dien 290 mg (0.73 m mol) of 3β-hydroxy-24-oxocholesta-5,7-dien and 122.5 mg (1.1 m mol) of potassium-t-butoxide were dissolved in a mixture of t-butyl alcohol and ethyleneglycol dimethyl ether (1:1 V/V) warming at 40° C., and while cooling the solution with ice-water to about 0° C. and stirring violently, 3β-hydroxy-24-oxocholesta-5,7-dien was oxidized with 8 c.c. of oxygen gas.

Water and ethyl acetate were added to separate the reaction mixture into layers.

The aqueous layers was extracted with ethyl acetate. The ethyl acetate extracts were combined with ethyl acetate layer, and the mixture was washed successively with a water, a dilute hydrochloric acid and a saturated aqueous solution of sodium hydrogen carbonate, dried over anhydrous sodium sulfate, filtered and conentrated.

The residue was dissolved in a mixture of 5 ml of benzene and 1 ml of ethyl acetate.

To the solution was added 48 mg of triphenyl phosphine, and the resulting hydroperoxide was reductively decomposed at room temperature for 30 minutes. The reaction mixture was concentrated, and the residue was chromatographed through a commercially available plate for preparative thinlayer chromatography (Silica gel as a carrier, a product of Merch Company, 20 cm×20 cm×0.5 mm) using an eluting solvent consisting of a mixture of benzene and ethyl acetate.

There was obtained 85 mg of 3β,25-dihydroxy-24-oxocholesta-5,7-dien having the following characteristics.

Melting point; 150°-152° C. (ethylacetate)

IR (KBr) cm$^{-1}$; 3400, 2940, 1710, 1460, 1375, 1060, 1035

NMR (CDCl$_3$, TMS), δ (ppm); 0.63 (3H, S, C-18-CH$_3$), 0.95 (3H, S, C-19-CH$_3$), 1.38 (6H, S, C-26-CH$_3$, C-27-CH$_3$), 3.4–3.7 (1H, bm, C-3-H), 5.30–5.66 (2H, bm, C-6-H, C-7-H)

U V (EtOH, $\lambda_{max}$)nm; 294 ($\epsilon$=6470), 282 ($\epsilon$=11270), 271 ($\epsilon$=10760), 262 ($\epsilon$=7840)

High resolution mass spectrum M+=414.3201 (C$_{27}$H$_{42}$O$_3$)

(v) Synthesis of 25-hydroxy-24-oxocholecalciferol;

157 mg of 3β,25-dihydroxy-24-oxocholesta-5,7-dien was dissolved in a mixture of ethyl alcohol (50 ml) and ether (500 ml), and this solution was irradiated thorugh a vycol filter with ultraviolet rays for 14 minutes at 5° C. in an atmosphere of argon using a 200 W high pressure mercury lamp (654A-36, trademark for a product of Hanovia Company.)

After the reaction, ether was evaporated off at about 30° C. under reduced pressure, 250 ml of benzene was added to the concentrated solution, and isomerization was carried out for 2.5 hours under reflux of benzene in an atmosphere of argon.

The reaction mixture was concentrated. The resulting residue was carefully separated by preparative thin-layer chromatography using a silica gel carrier which was immersed in a solution of silver nitrate in acetonitrile to impregnate it in an amount of about 2% by weight as silver nitrate and an eluting solvent consisting of a mixture of methyl alcohol and chloroform.

There were obtained 8.7 mg of 25-hydroxy-24-oxo previtamine D$_3$ and 14.8 mg of 25-hydroxy-24-oxo cholecalciferol having the following characteristics.

*25-hydroxy-24-oxo previtamine D$_3$

UV (EtOH)nm; $\lambda_{max}$ 260

*25-hydroxy-24-oxo cholecalciferol

UV (EtOH)nm; $\lambda_{max}$ 264.5 ($\epsilon$=15500), $\lambda_{min}$ 228 ($\epsilon$=8400)

IR (neet) cm$^{-1}$; 3375, 2925, 2860, 1705, 1385, 1045

NMR (CDCl$_3$, TMS), δ (ppm); 0.54 (3H, S, C-18-CH$_3$), 1.37 (6H, S, C-26-CH$_3$, C-27-CH$_3$), 3.90 (1H, b, C-3-H), 4.80, 5.03 (2H, m, C-19-H×2), 6.01, 6.20 (2H, AB quartet, J=11.5, C-6-H, (C-7-H).

High-resolution mass spectrum M+; 414.3131 (C$_{27}$H$_{42}$O$_3$)

Reference 3

Synthesis of 24,25-dihydroxy cholecalciferol;

4.9 mg of 25-hydroxy-24-oxo cholecalciferol was dissolved in 1 ml of methyl alcohol.

To the solution, 0.76 mg of sodium boron hydride was added. The mixture was stirred at room temperature for 20 minutes. After the reaction water was added, and the aqueous solution was extracted with ether. The ether extract was washed with a saturated aqueous solution of sodium chloride, dried over anhydrous sodium sulfate, filtered and concentrated. There was obtained about 5 mg of 24,25-dihydroxy cholecalciferol (quantitative yield).

This product showed the same analytical-thin-layer chromatography and high pressure liquid chromatography data as the authentic sample, and was identified as 24,25-dihydroxy cholecarciferol from the following spectrum data.

UV (Ether)nm; $\lambda$max 264, $\lambda_{min}$ 228

High resolution mass spectrum M+: 416.3413 ($C_{27}H_{44}O_3$)

EXAMPLE 9

(i) Synthesis of 24-ethylenedioxy-1α-hydroxy cholesterol;

1.36 g of 1α-hydroxy-24-oxo cholesterol was dissolved in 36 ml of anhydrous benzene. To the solution were added 9 ml of ethyleneglycol and 18 mg of p-toluen sulfonic acid. After the addition, the mixture was stirred and heated at a bath temperature of 105° C. for 20 hours in a flask equipped with receiver capable of measuring water in which was added a molecular sieve.

Water was added to separate the reaction mixture into layers. The aqueous layer was extracted with ethyl acetate.

The ethyl acetate extract was combined with the benzene layer, and the mixture was washed with a 5% aqueous solution of sodium hydrogen carbonate and a saturated aqueous solution of sodium chloride, dried over anhydrous sodium sulfate, filtered and concentrated.

The resulting solid product, 970 mg of 24-ethylenedioxy 1α-hydroxy cholesterol, without purification, was subjected to a acetylation reaction.

(ii) Synthesis of 24-ethylenedioxy-1α-hydroxy cholesterol-1α,3β-diacetate;

970 mg of 24-ethylenedioxy-1α-hydroxy cholesterol was dissolved in 3.3 ml of pyridine. To the solution was added 1.76 ml of acetic anhydride. The mixture was stirred and heated at a bath temperature of 80° C. for 3 hours.

After the reaction, water was added, and extracted with ether. The ether extract was washed successively with a 2N-hydrochloric acid, a 5% aqueous solution of sodium hydrogen carbonate and a saturated aqueous solution of sodium chloride, dried over anhydrous sodium sulfate, filtered and concentrated.

There was obtained 1.02 g of 24-ethylenedioxy-1α-hydroxy cholesterol 1α,3β-diacetate.

(iii) Synthesis of 1α,3β-dihydroxy-24-oxo cholesta-5,7-dien;

1.02 g of 24-ethylenedioxy-1α-hydroxy cholesterol-1α,3β-diacetate was dissolved in 30 ml of hexane. The solution was heated at a bath temperature of 95° C., stirred and to the solution 322 mg of 1,3-dibromo-5, 5-dimethyl hydantoine was added.

The mixture was stirred violently and heated under the irradiation with infrared rays for 15 minutes. The reaction mixture was cooled, and the resulting crystals were removed by filtration. The filtrate was concentrated at reduced pressure to afford a yellow oily substance, crude bromo-compounds of 24-ethylenedioxy-1α-hydroxy cholesterol 1α,3β-diacetate. To this substance was added 13 ml of xylene. The resulting solution was added dropwise over the course of about 15 minutes to a solution of 25 ml of xylene and 3.85 ml of s-collidine under reflux, and the reaction was performed for an additional 20 minutes. The reaction mixture was cooled, and the resulting crystals were removed by filtration.

The filtrate was concentrated at reduced pressure to afford a yellow oily substance, crude dehydro compounds of 24-ethylenedioxy-1α-hydroxy cholesterol-1α,3β-diacetate.

This substance was dissolved in 61 ml of acetone. To the solution, 357 mg of p-toluen sulfonic acid was added, and the mixture was stirred at room temperature for 2.5 hours. The mixture was concentrated. The resulting residue was dissolved in ethyl acetate, and the ethyl acetate solution was washed with a 5% aqueous solution of sodium hydrogen carbonate and a saturated aqueous solution of sodium chloride, dried over anhydrous sodium sulfate, filtered and concentrated to afford a crude residue containing 1α,3β-diacetoxy-24-oxo-cholesta-5,7-dien. This residue was dissolved in a mixture of benzene and methyl alcohol (46 ml, 1:1 V/V).

To the mixture, was added 27.5 ml of a 2 N-methyl alcohol solution of potassium hydroxide.

The mixture was stirred at a bath temperature of 60° C. for 3 hours.

The reaction mixture was concentrated, and water was added to separate into layers.

The aqueous layer was extracted with ethyl acetate. The ethyl acetate extract was combined with benzene layer, and the mixture was washed successively with a dilute hydrochloric acid and a saturated aqueous solution of sodium chloride, dried over anhydrous sodium sulfate, filtered and concentrated. The residue was chromatographed through a commercially available plate for preparative thin-layer chromatography (Silica gel, a product of Merch Company, 20 cm×20 cm×0.5 mm) which was immersed in a solution of silver nitrate in acetonitrile to impregnate it in an amount of about 2% by weight as silver nitrate.

There was obtained a purified product, 312 mg of 1α,3β-dihydroxy-24 oxo-cholesta-5,7-dien, having the following characteristics.

IR (KBr) cm$^{-1}$; 3450, 2960, 1718, 1475, 1387

NMR (CDCl$_3$, TMS), δ (ppm); 0.62 (3H, S, C-18-CH$_3$), 0.93 (3H, S, C-19-CH$_3$), 1.08 (6H, d, J=6 Hz, C-26-CH$_3$, C-27-CH$_3$), 3.74, 4.06 (2H, bm, C-1-H, C-3-H), 5.36, 5.68 (2H, bm, C-6-H, C-7-H)

(iv) Synthesis of 1α,3β,25-trihydroxy-24-oxo cholesta-5,7-dien;

248 mg (0.6 m mol) of 1α,3β-dihydroxy-24-oxo cholesta-5,7-dien and 101 mg (0.9 m mol) of potassium-t-butoxide was dissolved in a mixture of t-butyl alcohol and ethyleneglycol dimethyl ether (1:1 V/V) warming at 40° C., and while cooling the solution with icewater to about 0° C. and stirring violently.

1α,3β-dihydroxy-24-oxocholesta-5,7-dien was oxidized with 7 c.c. of oxygen gas.

After the reaction, water and ethyl acetate were added to separate the reaction mixture into layers. The aqueous layer was extracted with ethyl acetate. The ethyl acetate extracts were combined with ethyl acetate layer, and the mixture was washed successively with a water, a dilute hydrochloric acid and a saturated aqueous solution of sodium hydrogen carbonate, dried over anhydrous sodium sulfate, filtered and concentrated.

The residue was dissolved in a mixture of benzene and ethyl acetate (5:1 V/V).

To the solution, was added 40 mg of triphenyl phosphine, and the resulting hydroperoxide was reductively decomposed at room temperature for 30 minutes.

The reaction mixture was concentrated, and the residue was chromatographed through a commercially available plate for preparative thin-layer chromatography (Silica gel as a carrier, a product of Merch Company, 20 cm×20 cm×0.5 mm) using an eluting solvent consisting of a mixture of benzene and acetone. There was obtained 88 mg of 1α,3β25-trihydroxy-24-oxo cholesta-5,7-dien having the following characteristics.

Melting point; 162.5°–164° C. (methylalcohol)

IR (KBr) cm$^{-1}$; 3450, 2975, 1715, 1468, 1382, 1060, 1045

NMR (CDCl$_3$, TMS), δ (ppm); 0.63 (3H, S, C-18-CH$_3$), 0.94 (3H, S, C-19-CH$_3$), 1.38 (6H, S, C-26-CH$_3$, C-27-CH$_3$), 3.74, 4.06 (2H, bm, C-1-H, C-3H), 5.36, 5.68 (2H, bm, C-6-H, C-7-H)

UV (EtOH, λ$_{max}$)nm ; 294 (ε=6160), 282 (ε=10550), 271 (ε=9810), 263 (ε=6840)

High resolution mass spectrum; M$^+$: 430.3122 (C$_{27}$H$_{42}$O$_4$)

Reference 4

Synthesis of 1α,25-dihydroxy-24-oxo cholecalciferol;

70 mg of 1α,3β,25-trihydroxy-24-oxo cholesta-5,7-dien was dissolved in a mixture of ethyl alcohol (50 ml) and ether (500 ml), and this solution was irradiated through a vycol filter with ultraviolet rays for 7 minutes at about 10° C. in an atmosphere of argon using a 200 W high pressure mercury lamp (654A-36, trademark for a product of Hanovia Company.)

After the reaction, ether was evaporated off at about 30° C. under reduced pressure. 250 ml of benzene was added to the concentrated solution, and isomerization was carried out for 2.5 hours under reflux of benzene in an atmosphere of argon.

The reaction mixture was concentrated. The resulting residue was carefully separated successively by preparative thin-layer chromatography using a silica gel carrier which was immersed in a solution of silver nitrate in acetonitrile to impregnate it in an amount of about 2% by weight as silver nitrate, and an eluting solvent consisting of a mixture of methyl alcohol and dichloromethane, and by preparative thin-layer chromatography using a silica gal carrier and an eluting solvent consisting of a mixture of benzene and acetone.

There was obtained 10.8 mg of 1α,25-dihydroxy-24-oxo cholecalciferol having the following characteristics.

Melting point; 91°–93.5° C.

Ir (KBr) cm$^{-1}$; 3450, 2960, 1715, 1390, 1055

NMR (CDCl$_3$, TMS), δ (ppm); 0.55 (3H, S, C-18-CH$_3$), 1.37 (6H, S, C-26-CH$_3$, C-27-CH$_3$), 4.98, 5.30 (2H, m, C-19-H×2), 6.18 (2H, AB quartet, J=11.5 Hz, C-6-H, C-7-H)

UV (Ether)nm; λ$_{max}$ 264.5, λ$_{min}$ 228.6

High resolution mass spectrum; M$^{30}$:430.3116 (C$_{27}$H$_{42}$O$_4$)

Reference 5

Effect of 25-hydroxy-24-oxo cholecalciferol to promote calcium absorption from the intestinal tract;

Comparatison with 1α,25-dihydroxy cholecalciferol; Weanling Wistar male rats (with a body weight of about 100 g) which had been fed only with vitamin D-deficient diet for 6 weeks were fasted overnight. A solution of 25-hydroxy-24-oxo cholecalciferol (250 ng/head) in a 1:1 mixture of ethyl alcohol and physiological saline solution or a solution of 1α,25-dihydroxy cholecalciferol (250 ng/head) in the same mixture was intravenously administered to the rats. They were killed 4 hour, 8 hour, 24 hour and 48 hour later, and calcium absorption at the intestinal tube was measured by the everted gut sac method [see Martin, D. L. and Deluca, H. F., Amer, J. Physiol. 216, 1351 (1969)]. The results are shown in FIG. 1.

It is seen from the experimental results that 1α,25-dihydroxy cholecalciferol showed the maximum effect after about 8 hours of the administration and the effect was decreasing urgently from then, while 25-hydroxy-24-oxo-cholecalciferol showed the effect after about 4 hours of the administration and the effect continued for 44 hours.

Reference 6

Combination of 1α,25-dihydroxy-24-oxo cholecalciferol with the 1α,25-dihydroxy cholecalciferol-receptor in the chick's intestinal tube;

It is well known that the combination ability of vitamin D analogue with the 1α,25-dihydroxy cholecalciferol-receptor was relative to the strength of the effect to promote calcium absorption from the intestinal tract. And so the combination ability of 1α,25-dihydroxy-24-oxo cholecalciferol with the 1α,25-dihydroxy cholecalciferol-receptor in the chick's intestinal tube was investigated by the authentic method [see, for example, Steroids. 30, 2, 245–257 (1977)].

There was obtained the results shown in Table 1.

TABLE 1

| Vitamine D$_3$ analogue | 50% Displacement (pg) | Molar ratio |
|---|---|---|
| 1α,25-dihydroxy cholecarciferol | 46 | 1 |
| 1α,25-dihydroxy-24-oxo-cholecarciferol | 138 | 3 |

It is seen from these results that 1α,25-dihydroxy-24-oxo cholecalciferol was expected to have the active vitamine D$_3$-effects.

What we claim is:

1. A 25-hydroxy-24-oxocholestane derivative of the following formula (1)

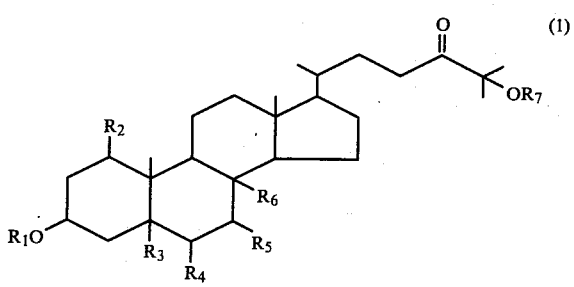

wherein R$_1$ is a hydrogen atom or a hydroxyl protective group; R$_2$ is a hydrogen atom, a hydroxy group or a protected hydroxy group; R$_3$ is a hydrogen atom, R$_4$ is a hydrogen atom, a hydroxy group or a protected hydroxy group; or R$_3$ and R$_4$, taken together may form a carbon-carbon bond; R$_5$ and R$_6$ are a hydrogen atom, or R$_5$ and R$_6$ may together form a carbon-carbon bond; R$_7$ is a hydrogen atom or a hydroxyl protective group.

2. The 25-hydroxy-24-oxocholestane derivative of claim 1, which is expressed by the following formula (1-1)

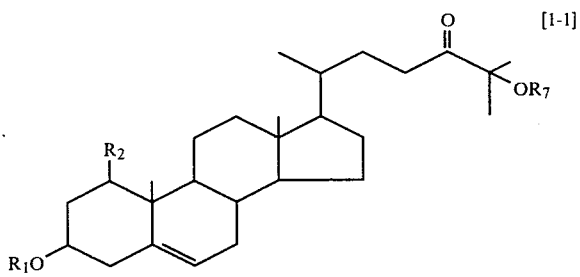

wherein $R_1$, $R_2$ and $R_7$ are the same as defined in claim 1.

3. The 25-hydroxy-24-oxocholestane derivative of claim 1, which is expressed by the following formula (1-2)

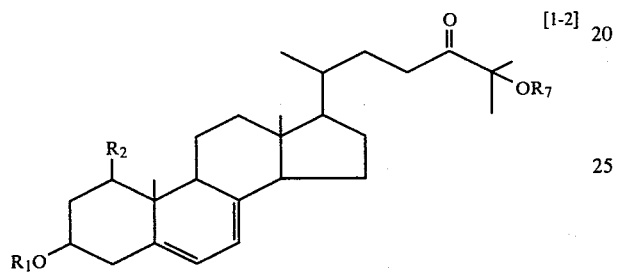

wherein $R_1$, $R_2$ and $R_7$ are the same as defined in claim 1.

4. The 25-hydroxy-24-oxocholestane derivative of claim 1, which is expressed by the following formula (1-3)

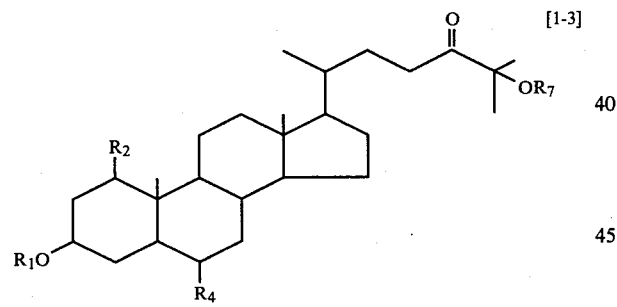

wherein $R_1$, $R_2$, $R_4$ and $R_7$ are the same as defined in claim 1.

5. A process for preparing a 25-hydroxy-24-oxocholestane derivative expressed by the following formula (1)

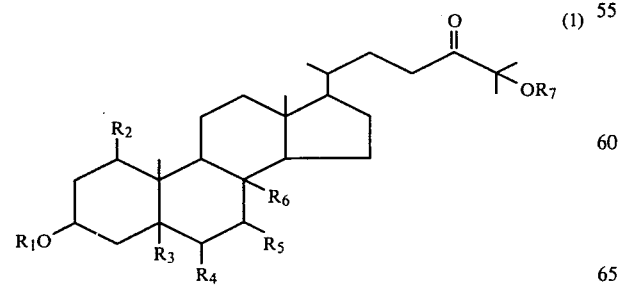

wherein $R_1$ is a hydrogen atom or a hydroxyl protective group; $R_2$ is a hydrogen atom, a hydroxy group or a protected hydroxy group; $R_3$ is a hydrogen atom, $R_4$ is a hydrogen atom, a hydroxy group or a protected hydroxy group, or $R_3$ and $R_4$, taken together, may form a carbon-carbon bond; $R_5$ and $R_6$ are a hydrogen atom, or $R_5$ and $R_6$ may together form a carbon-carbon bond; $R_7$ is a hydrogen atom or a hydroxyl protective group, which comprises oxidizing a 24-oxocholestane derivative of the formula (2)

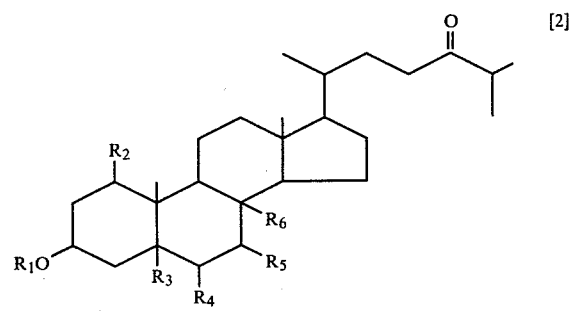

wherein $R_1$, $R_2$, $R_3$, $R_4$, $R_5$ and $R_6$ are the same as defined above
with molecular oxygen or a molecular oxygen-containing gas under basic conditions and (i) where required, splitting off hydroxyl protective groups, or (ii) where required, protecting hydroxy groups with a hydroxyl protective group.

6. The process of claim 5, wherein the 24-oxo-cholestane derivative is a compound of the formula (2-1)

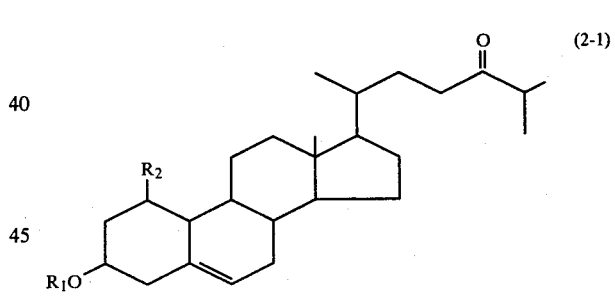

wherein $R_1$ and $R_2$ are the same as defined in claim 5.

7. The process of claim 5, wherein the 24-oxocholestane derivative is a compound of the formula (2-2)

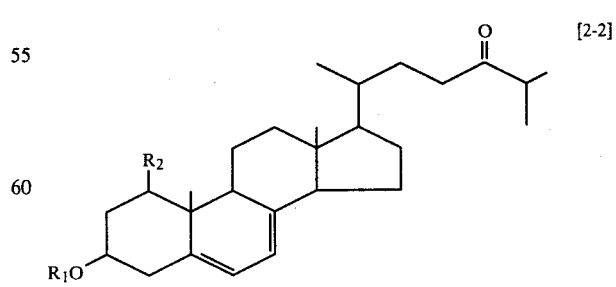

wherein $R_1$ and $R_2$ are the same as defined in claim 5.

8. The process of claim 5 wherein the 24-oxocholestane derivative is a compound of the formula (2-3)

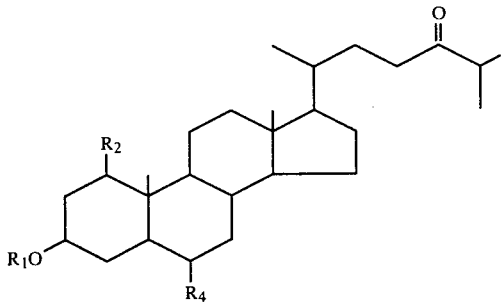

wherein $R_1$, $R_2$ and $R_4$ are the same as defined in claim 5.

9. The process of claim 5, 6, 7 or 8, wherein said basic conditions are provided by a lower alcoholate.

10. The process of claim 5, 6, 7 or 8, wherein the amount of the reagent used to provide basic conditions is 1 to 10 moles per mole of the 24-oxocholestane derivative.

11. The process of claim 5, 6, 7 or 8, wherein the oxidation is carried out with molecular oxygen.

12. A process for preparing a 25-hydroxy-24-oxocholestane derivative expressed by the following formula (1)

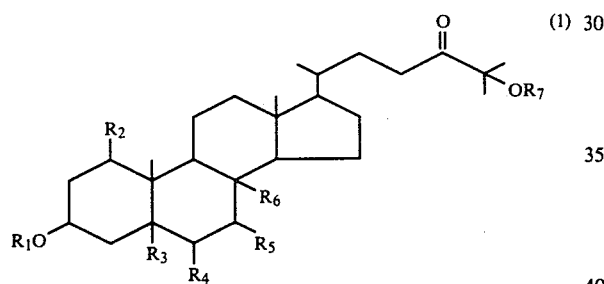

wherein $R_1$ is a hydrogen atom or a hydroxyl protective group; $R_2$ is a hydrogen atom, a hydroxy group or a protected hydroxy group; $R_3$ is a hydrogen atom, $R_4$ is a hydrogen atom, a hydroxy group or a protected hydroxy group, or $R_3$ and $R_4$, taken together, may form a carbon-carbon bond; $R_5$ and $R_6$ are a hydrogen atom, or $R_5$ and $R_6$ may together form a carbon-carbon bond; $R_7$ is a hydrogen atom or a hydroxyl protective group which comprises reducing, with a metal or a nucleophilic reagent, a 25-hydroperoxy-24-oxocholestane derivative of the formula (3)

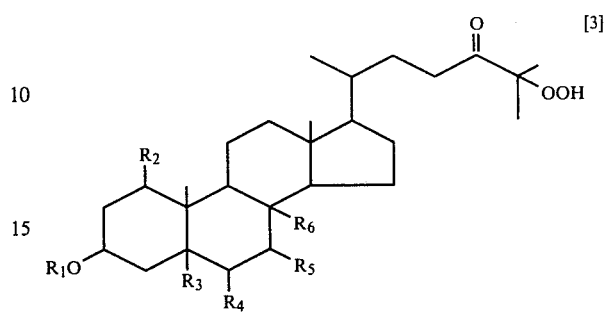

wherein $R_1$, $R_2$, $R_3$, $R_4$, $R_5$ and $R_6$ are the same as defined above, and (i) where required, splitting off hydroxyl protective groups, or (ii) where required, protecting hydroxy groups with a hydroxyl protective group.

13. A process for preparing a 25-hydroperoxy-24-oxocholestane derivative of the formula (3)

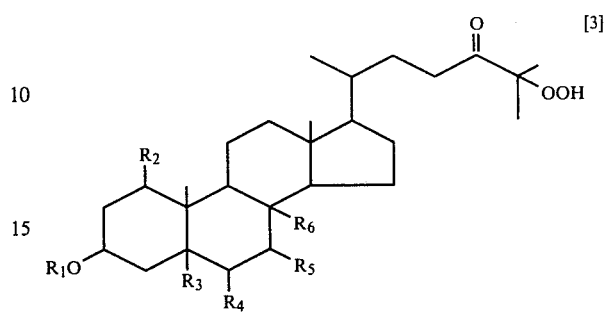

wherein $R_1$ is a hydrogen atom or a hydroxyl protective group; $R_2$ is a hydrogen atom, a hydroxy group or a protected hydroxy group; $R_3$ is a hydrogen atom, $R_4$ is a hydrogen atom, a hydroxy group or a protected hydroxy group, or $R_3$ and $R_4$, taken together, may form a carbon-carbon bond; $R_4$ and $R_6$ are a hydrogen atom, or $R_5$ and $R_6$ may together form a carbon-carbon bond; $R_7$ is a hydrogen atom or a hydroxyl protective group which comprises oxidizing a 24-oxocholestane derivative of the formula (2)

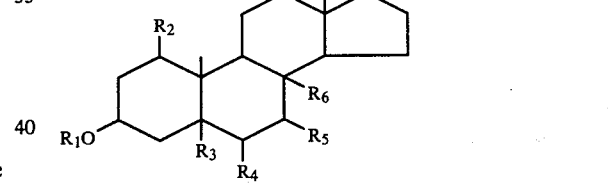

wherein $R_1$, $R_2$, $R_3$, $R_4$, $R_5$ and $R_6$ are the same as defined above
with molecular oxygen or a molecular oxygen-containing gas under basic conditions.

14. The process of claim 13 wherein said basic conditions are provided by a lower alcoholate.

15. The process of claim 13 or 14 wherein the amount of the reagent used to provide basic conditions is 1 to 10 moles per mole of the 24-oxocholestane derivative.

16. A process for preparing a 25-hydroxy-24-oxocholestane derivative expressed by the following formula (1)

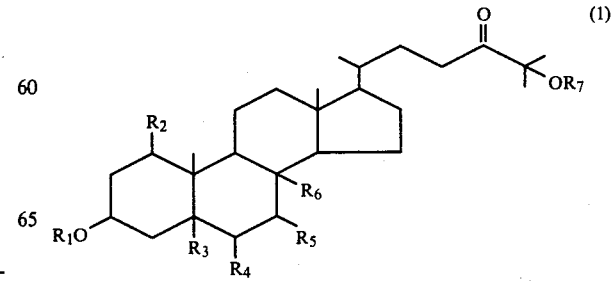

wherein $R_1$ is a hydrogen atom or a hydroxyl protective group; $R_2$ is a hydrogen atom, a hydroxy group or a protected hydroxy group; $R_3$ is a hydrogen atom, $R_4$ is a hydrogen atom, a hydroxy group or a protected hydroxy group, or $R_3$ and $R_4$, taken together, may form a carbon-carbon bond; $R_5$ and $R_6$ are a hydrogen atom, or $R_5$ and $R_6$ may together form a carbon-carbon bond; $R_7$ is a hydrogen atom or a hydroxyl protective group which comprises oxidizing a 24-oxocholestane derivative of the following formula (2)

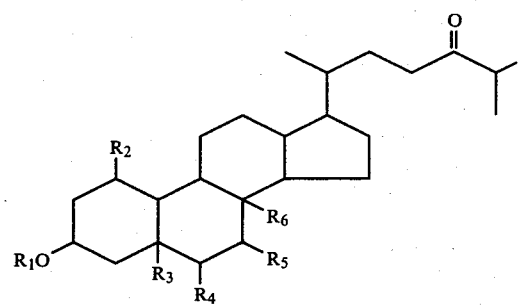

wherein $R_1$, $R_2$, $R_3$, $R_4$, $R_5$ and $R_6$ are the same as defined above
with molecular oxygen or a molecular oxygen-containing gas to form a 25-hydroperoxy-24-oxocholestane derivative of the following formula (3)

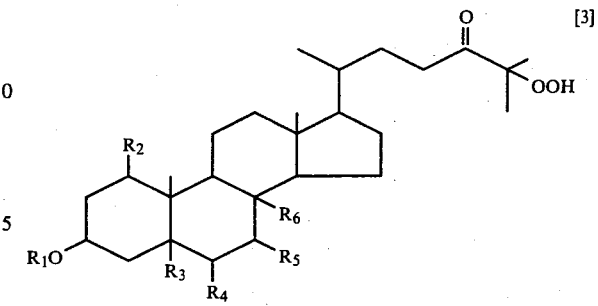

wherein $R_1$, $R_2$, $R_3$, $R_4$, $R_5$ and $R_6$ are the same as defined above
then reducing, with a metal or a nucleophilic reagent, and (i) where required, splitting off hydroxyl protective groups or (ii) where required, protecting hydroxy groups with a hydroxyl protective group.

* * * * *